United States Patent [19]

Lemke

[11] Patent Number: 4,934,789

[45] Date of Patent: Jun. 19, 1990

[54] LENS MOUNTING FOR A VARIFOCAL LENS FOR TV CAMERAS

[76] Inventor: Norbert Lemke, Veilcvenstrasse 10, 8031 Puchheim, Fed. Rep. of Germany

[21] Appl. No.: 300,066

[22] PCT Filed: Mar. 31, 1988

[86] PCT No.: PCT/DE88/00213

§ 371 Date: Nov. 30, 1988

§ 102(e) Date: Nov. 30, 1988

[87] PCT Pub. No.: WO88/07694

PCT Pub. Date: Oct. 10, 1988

[30] Foreign Application Priority Data

Mar. 31, 1987 [DE] Fed. Rep. of Germany ....... 3710646

[51] Int. Cl.$^5$ .............................................. G02B 7/04
[52] U.S. Cl. ..................................... 350/255; 350/257
[58] Field of Search ............... 350/252, 255, 257, 254, 350/427, 429

[56] References Cited

U.S. PATENT DOCUMENTS

| 1,760,827 | 5/1930 | Goldhammer . | |
|---|---|---|---|
| 2,643,581 | 6/1953 | Wehrenfennig | 350/257 |
| 3,744,884 | 7/1973 | Filipovich et al. | 350/255 |
| 4,030,113 | 6/1977 | Obreschkow | 350/255 |
| 4,307,951 | 12/1981 | Saito et al. | 350/255 |
| 4,307,954 | 12/1981 | Ludwig | 350/257 |
| 4,585,313 | 4/1986 | Iwata et al. | 350/255 |
| 4,639,772 | 1/1987 | Sluyter et al. | 358/98 |
| 4,659,203 | 4/1987 | Niwa et al. | 350/257 |
| 4,822,153 | 4/1989 | Tomori et al. | 350/255 |

FOREIGN PATENT DOCUMENTS 1459104 11/1966 France .
61-18910 1/1986 Japan .

OTHER PUBLICATIONS

Davey et al, "Zoom Lens Mount," *Research Disclosure*, No. 116, Dec. 1973, pp. 57-58, No. 11644.

*Primary Examiner*—Bruce Y. Arnold
*Assistant Examiner*—Martin Lerner
*Attorney, Agent, or Firm*—Evenson, Wands, Edwards, Lenahan & McKeown

[57] ABSTRACT

Described is a varifocal lens for a TV camera, which in particular may be mounted on an endoscope, having a lens barrel, which is provided with guide indentations for radial pins attached to the lens mountings, and two lens groups, which may be moved toward each other for setting the focal length and together for focussing. The invented lens is distinguished by the combination of the following features:

said lens barrel is guided in a support bearing in the direction of the optical axis in such a manner that it can be moved and is secured against rotary motion.

the guide indentations are slits, which are open at the front or the rear and consist of a straight section running parallel to said optical axis and abutting upon the front or rear end of the barrel; a section running concentrically to said optical axis and a hereto abutting actual cam for controlling the movement of the lens groups.

arranged in a rotary manner on said lens barrel is a second barrel, the inner surface of which is provided with indentations which run parallel to said optical axis and with which the pins engage.

12 Claims, 1 Drawing Sheet

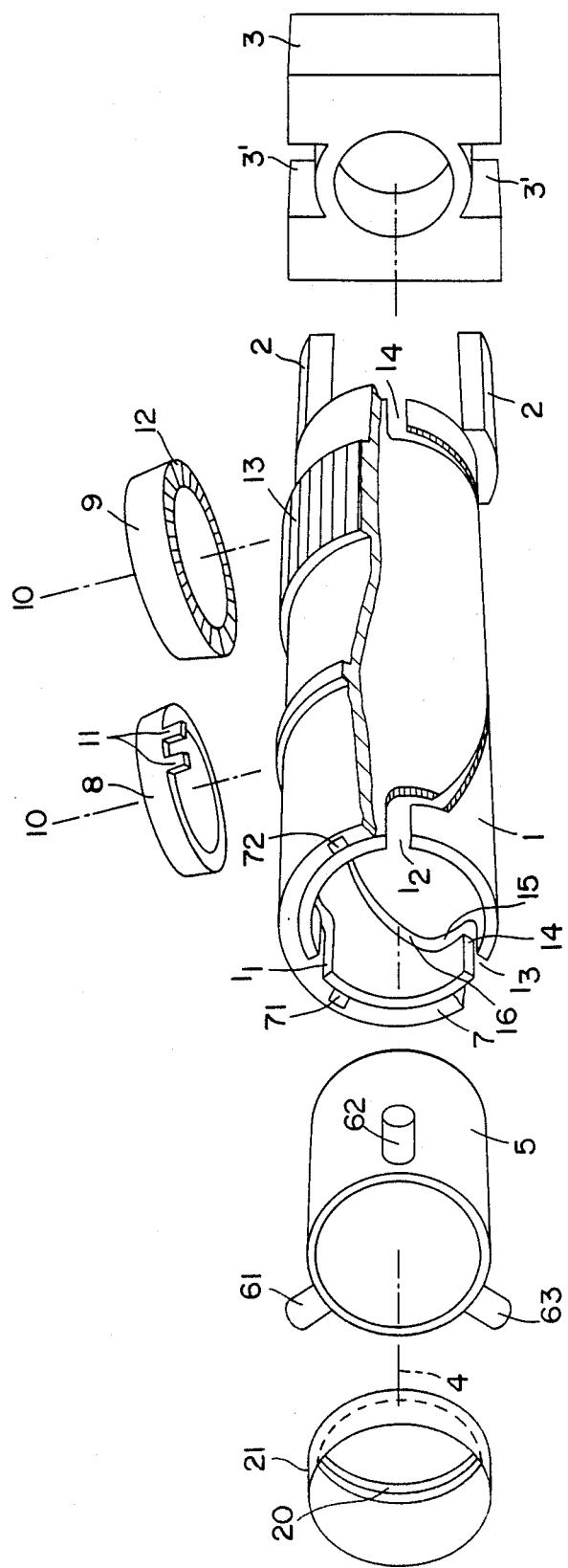

LENS MOUNTING FOR A VARIFOCAL LENS FOR TV CAMERAS

BACKGROUND AND SUMMARY OF THE PRESENT INVENTION

1. Field of the Invention

The present invention relates to a varifocal lens for a TV camera which in particular may be mounted on an end scope, having a lens barrel, which is provided with guide indentations for radial pins may be moved toward each other for setting the focal length and together for focussing.

By way of illustration, TV cameras have increasingly been employed for taking endoscopic pictures. Such TV cameras must be as small and lightweight as possible in order not to hamper the physician during the operation. TV cameras with varifocal lenses, which would permit adjustment of the field of vision and adaption to various instruments have, for this reason, only been proposed now and again without having had any particular impact in practice.

An object of the present invention is to provide as small and light as possible a varifocal lens for a TV camera, which is particularly meant to be mounted on an endoscope.

An inventive solution to the object of the present invention and its further embodiments is described in the following.

An inventive step is that the lens barrel is guided in a support bearing, which is fixed in relation to the encasement of the TV camera, in such a manner that it can be moved in the direction of the optical axis of the lens and is secured to prevent rotary motion. Furthermore, the guide indentations are slits, which are open at the front and at the back and consist of a straight section abutting upon the front or rear end of the barrel and running parallel to the optical axis, a section running concentrically to the optical axis, and the hereto abutting actual cam for controlling the movement of the lens groups.

As a result the following advantages are yielded:

The lens mounting can be inserted into the lens barrel through the front or rear slits in such a manner that the lens barrel does not have to be constructed out of two half shells that consequently would have to be securely joined by means of a medium, thereby increasing the diameter. The support bearing, which prevents rotary motion while permitting moving the lens for focussing, does not increase the diameter of the varifocal lens.

Due to the one-piece construction of the lens barrel, it suffices to arrange onto the lens barrel a second barrel in such a manner that it can be rotated, the inner surface of which is provided with indentations running parallel to the optical axis for the pins to engage. The focal length of the varifocal lens can easily be set by turning this second barrel.

For varying the focal length, the second barrel may, of course, be turned manually or by means of a setting lever.

However, it is particularly advantageous if a tooth system is provided on the outer surface of the second barrel, which meshes together with a castellated wheel, as in this manner a simple knurled wheel on the outer side of the varifocal lens is all that is needed for setting the focal length permitting, as opposed to a setting ring that runs concentrically to the optical axis, easy one-handed operation for setting both the focal length as well as focussing. The knurled wheel for focussing may, by way of illustration, engages the eccentric, elliptical indentations in the second barrel by means of pins.

The stability of the slit lens barrel and a steadiness of the setting are substantially increased by means of the further embodiment wherein the lens mountings, on the one hand, give the lens barrel stability and, on the other hand, as a result of this embodiment they cannot tip.

A further embodiment described in claim 4 hereto, which is provided with two lugs that run parallel to the optical axis, makes very compact assembly possible as the support bearing can be provided at the point of separation between the lens and the tube for the TV camera, where it takes up practically no additional room.

Yet a further embodiment, which is provided with knurled wheels for focussing as well as for setting the focal length, is ergonomically advantageous, as it makes one-hand operation possible without changing the lever position.

A water protection rim also contributes to solving the object to of the present invention as no measures that would increase volume or weight, like those required according to the state of the art, are needed when flanging the varifocal lens to an endoscope in order to prevent water from running onto the front cover.

BRIEF DESCRIPTION OF THE SINGLE FIGURE

The present invention is made more apparent in the following section using a preferred embodiment with reference to the accompanying drawing whose single figure shows the mounting of an invented varifocal lens in perspective and separated.

DETAILED DESCRIPTION OF THE PREFERRED EMBODIMENT

The invented lens is provided with a lens barrel 1 having two lugs 2 by means of which it is guided and moved in the direction of the optical axis 4 in a support bearing 3 by means of indentation or slits 3'.

Two lens groups are guided and moved longitudinally in lens barrel 1 in order to set the focal length of the lens. For this purpose, the lens groups are provided with lens mountings 5, of which only the front one is illustrated in the figure. Each of the lens mountings 5 has three pins 61 to 63 running radially, which pass through the cams designed as slits $1_1$ to $1_6$ in lens barrel 1 and engage in grooves 71, 72, ... in a second barrel 7, which is arranged on lens barrel 1 in a rotary manner.

Furthermore, two wheels 8 and 9, the rotary axis 10 of which is situated vertically on the optical axis 4 of the lens, are provided for focussing and setting the focal length.

Wheel 8, which is intended for focussing, is provided with pins 11, which mesh together with an eccentric, elliptical indentation in the second barrel 7. In this manner, the varifocal lens, which is guided and moved in support bearing 3, can be moved longitudinally along its optical axis 4 by turning wheel 8.

A castellated tooth system 12 is provided on the underside of the second wheel 9, which meshes together with a tooth system 13 provided on the second barrel 7. In this fashion the second barrel 7 on the lens barrel may be turned by means of the second wheel 9 in such a manner that the lens groups move corresponding to the cams for setting the focal length.

Slits $1_1$ to $1_6$ serving as cams for the lens groups are composed of three sections: a section 14, which runs parallel to the optical axis 4 and permits inserting the lens mounting; a section 15, which runs concentrically to the optical lens and prevents the lens mounting from being turned out of the cam by continued turning of the second barrel 7; and an actual cam 16, which controls the movement of the lens groups when setting the focal length.

In the preceeding section, the present invention has been described using a preferred embodiment without the intention of limiting the scope of th overall inventive idea-to create a lens, with which the lens mounting can be inserted into the control barrel without constructing the latter out of two half shells. Of course, there are a great variety of possible alterations and modifications within the scope of the overall inventive idea:

By way of illustration, setting the focal length may also occur by means of turning the second barrel itself.

Moreover, it is possible to attach the invented lens mounting for the varifocal lens undetachably directly to the camera or detachably via bayonet or C-mount joints.

Furthermore, the construction of the lenses of the individual lens groups can for the most part be freely selected.

The varifocal lens constructed according to the present invention is already very compact due to the special construction of the lens mounting. Further reduction of the weight and of the dimensions is achieved by the fact that each lens group is composed only of one cement section. In accordance with the invention, it became apparent that this type of construction suffices for a TV camera for taking endoscopic pictures.

Furthermore, a water protection rim 20, which prevents water from running onto a front cover 21 and, by way of illustration, makes scavenging air fitting superfluous, may be provided at the front cover when employing the invented varifocal lens together with an endoscope.

I claim:
1. A varifocal lens having an optical axis comprising:
   two lens groups which are moved relative to one another to set a focal length of the lens and are moved together to focus the lens;
   lens mountings for separately mounting each of the lens groups, each mounting having radial pins;
   a lens barrel guided in a support bearing for movement along the optical axis and having guide indentations in the form of slits for receiving the radial pins of each of the lens mountings, the slits being open at a front and rear of the lens barrel for receiving the radial pins of the lens mountings to permit insertion of each of the lens groups into the lens barrel, the slits comprising a straight section running parallel to the optical axis which abuts the front and rear of the lens barrel as well as a second section running concentrically to the optical axis and a cam section abutting the second section for controlling movement of the lens groups;
   a second barrel arranged in a rotary manner on the lens barrel for rotation about a rotary axis, an inner surface thereof having indentations running parallel to the optical axis which engage the radial pins of each of the lens mountings.
   whereby relative rotary movement between the lens barrel and the second barrel moves the two lens groups relative to one another to set the focal length and movement of the lens barrel in the support bearing moves the lens groups to set the focusing.

2. A varifocal lens as described in claim 1, wherein an outer surface of the second barrel is provided with a tooth system, which meshes together with a castellated wheel, for setting the focal length due to relative movement of the lens groups with respect to one another.

3. A varifocal lens as described in claim 2, wherein each lens mounting is provided with three pins spaced 120° apart, which engage with the corresponding guide slits and indentations on the inner side of the second barrel.

4. A varifocal lens according to claim 3, wherein the varifocal lens is for a TV camera.

5. A varifocal lens according to claims 3, wherein the lens is for a TV camera mounted on an endoscope.

6. A varifocal lens as described in claim 3, wherein said lens barrel is provided with two lugs which run parallel to the optical axis and are inserted in complementary slits or indentations in said support bearing.

7. A varifocal lens as described in claim 6, wherein knurled wheels, the rotary axis of each of which is vertical to said optical axis, are provided for focussing and resetting the focal length.

8. A varifocal lens as described in claims 7, wherein the front cover of said lens is provided with a water protection rim around it.

9. A varifocal lens as described in claim 1, wherein each lens mounting is provided with three pins spaced 120° apart, which engage with the corresponding guide slits and indentations on the inner surface of the second barrel.

10. A varifocal lens as described in claim 1, wherein said lens barrel is provided with two lugs which run parallel to the optical axis and are inserted in complementary slits or indentations in said support bearing.

11. A varifocal lens as described in claim 1, wherein knurled wheels the rotary axis of each of which is vertical to said optical axis, are provided for focussing and resetting the focal length.

12. A varifocal lens as described in claim 1, wherein a front cover of said lens is provided with a water protection rim around it.

* * * * *